(12) United States Patent
Hong

(10) Patent No.: US 10,888,289 B2
(45) Date of Patent: Jan. 12, 2021

(54) MAMMOGRAPHY APPARATUS

(71) Applicant: VIEWORKS CO., LTD., Anyang-Si (KR)

(72) Inventor: Soon Gil Hong, Chungcheongnam-do (KR)

(73) Assignee: VIEWORKS CO., LTD., Anyang-Si (KR)

(*) Notice: Subject to any disclaimer, the term of this patent is extended or adjusted under 35 U.S.C. 154(b) by 160 days.

(21) Appl. No.: 16/193,264

(22) Filed: Nov. 16, 2018

(65) Prior Publication Data
US 2019/0150866 A1    May 23, 2019

(30) Foreign Application Priority Data

Nov. 17, 2017  (KR) .................. 10-2017-0154293

(51) Int. Cl.
*A61B 6/00* (2006.01)
*A61B 6/04* (2006.01)

(52) U.S. Cl.
CPC .......... *A61B 6/4476* (2013.01); *A61B 6/4452* (2013.01); *A61B 6/502* (2013.01); *A61B 6/0414* (2013.01); *A61B 6/54* (2013.01); *A61B 6/56* (2013.01)

(58) Field of Classification Search
CPC ..... A61B 6/4476; A61B 6/502; A61B 6/4452; A61B 6/0414; A61B 6/54; A61B 6/56
See application file for complete search history.

(56) References Cited

U.S. PATENT DOCUMENTS

| | | | | |
|---|---|---|---|---|
| 9,829,055 B2 * | 11/2017 | Defosse | ................ | H02K 7/112 |
| 2008/0000730 A1 * | 1/2008 | Port-Robach | ....... | F16H 25/2454 |
| | | | | 188/71.2 |
| 2009/0247364 A1 * | 10/2009 | Sano | .................. | F16H 25/2021 |
| | | | | 477/197 |
| 2013/0313067 A1 * | 11/2013 | Finney | .................... | F16D 55/02 |
| | | | | 192/223.2 |
| 2016/0261096 A1 * | 9/2016 | Nikodem | ............. | H02B 11/127 |

FOREIGN PATENT DOCUMENTS

KR    10-2014-0118443 A    10/2014

* cited by examiner

*Primary Examiner* — David J Hlavka
(74) *Attorney, Agent, or Firm* — Osha Bergman Watanabe & Burton LLP

(57) ABSTRACT

Disclosed herein is a mammography apparatus including a driving shaft configured to transmit power to a transfer unit, a loader configured to be driven by receiving power from a driving unit, a power transmission unit coupled to one end of the driving shaft and configured to selectively come in contact with the loader due to an external force, an emergency braking unit coupled to the other end of the driving shaft to be driven together with the driving shaft, and configured to stop being driven when power supply is cut off, and a driving controller provided between the driving shaft and the emergency braking unit so that a direction in which the driving shaft is driven is restricted to one direction.

7 Claims, 7 Drawing Sheets

MAMMOGRAPHY APPARATUS

CROSS-REFERENCE TO RELATED APPLICATION

This application claims priority to and the benefit of Korean Patent Application No. 10-2017-0154293, filed on Nov. 17, 2017, the disclosure of which is incorporated herein by reference in its entirety.

BACKGROUND

1. Field of the Invention

The present invention relates to a mammography apparatus, and more particularly, to a mammography apparatus in which a pressure unit is released from a subject in case of emergency so that an accident occurring to the subject is prevented.

2. Discussion of Related Art

Generally, mammography has been rapidly spread due to, in addition to various advantages of radiation, specifically X-ray image technology, its unique characteristic in that exposure is minimized through image enlargement, reduction in number of shots, increase in resolution, and adjustment of brightness and contrast ratio.

A mammography apparatus includes a column configured to stand upright on a floor, a C-arm having a C-shape or a shape similar thereto as a whole due to both ends bent in an arc shape to face each other while an intermediate portion is connected to be liftable/lowerable and rotatable along the column, a generator mounted on one end of the C-arm and configured to radiate X-rays toward the other end facing the one end, a detector configured to face the generator, and a pressure detector configured to face the generator, and a pressure pad configured to linearly reciprocate between the generator and the detector along an inner surface of the C-arm.

The pressure pad is lifted and lowered using a driving unit and applies direct pressure to a measurement subject, specifically a breast, with a set load according to an electrical signal.

In a conventional case in which power supplied to a mammography apparatus for driving the same is cut off due to sudden power blackouts, there is a problem in that a pressure pad falls freely toward a breast placed on an examination plate, continuously presses the breast, and causes pain.

The related art of the present invention has been disclosed in Korean Patent Publication No. 10-2014-0118443 (Date of Publication: Oct. 8, 2014, Title of Invention: MAMMOGRAPHY APPARATUS AND POSITION ALIGNMENT CONTROL METHOD THEREOF).

SUMMARY OF THE INVENTION

The present invention has been devised to solve the above problem, and the present invention is directed to providing a mammography apparatus in which a pressure unit is released from a subject in case of emergency, such as when power supply is cut off due to a driving controller, so that an accident occurring to the subject is prevented.

A mammography apparatus according to the present invention includes a driving shaft configured to transmit power to a transfer unit, a loader configured to be driven by receiving power from a driving unit, a power transmission unit coupled to one side of the driving shaft and configured to selectively come in contact with the loader due to an external force, an emergency braking unit coupled to the other side of the driving shaft to be driven together with the driving shaft, and configured to stop being driven when power supply is cut off, and a driving controller provided between the driving shaft and the emergency braking unit so that a direction in which the driving shaft is driven is restricted to one direction.

The emergency braking unit may include a housing provided in a main body, a braking shaft configured to be rotatable inside the housing and connected to the driving shaft, and a braking main body coupled to the braking shaft and configured to rotate together with the braking shaft, wherein, when power supply is cut off, the braking main body moves toward the housing and comes into contact with the housing.

An insertion part may be formed in the braking shaft, the driving shaft may be disposed inside the insertion part, and the driving controller may be provided between the braking shaft and the driving shaft.

The driving controller may include a fixed part coupled to an inner surface of the braking shaft, and a rotary part coupled to the driving shaft and configured to only rotate in one direction inside the fixed part.

A coupling protrusion may be formed to protrude along an inner circumferential surface of the rotary part, and a coupling groove may be formed along an outer circumferential surface of the driving shaft to correspond to the shape of the coupling protrusion.

The mammography apparatus may further include a first supporter disposed to be spaced apart from the driving controller and provided between the insertion part and the driving shaft.

The mammography apparatus may further include a second supporter provided in the main body, the driving shaft is connected to one end of the braking shaft, and the second supporter is coupled to the other side of the braking shaft.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
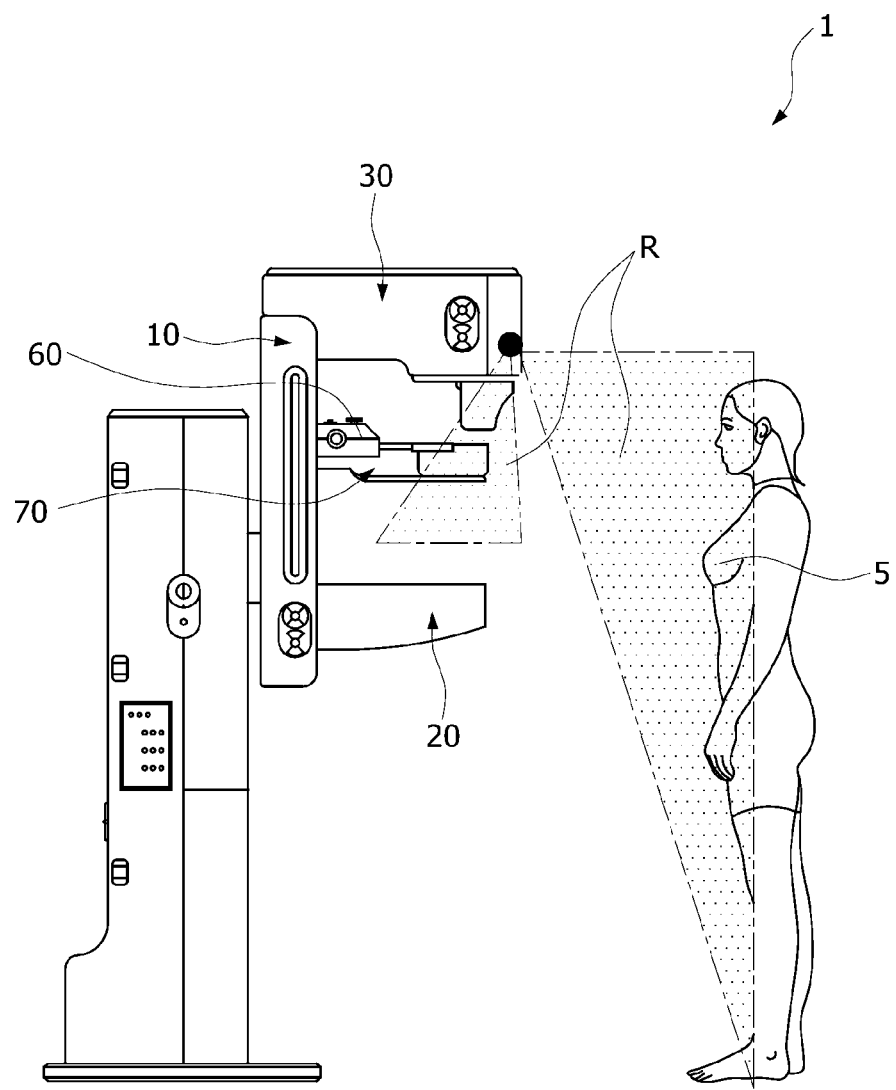
FIG. 1 is a side view illustrating a mammography apparatus according to an embodiment of the present invention.

Hereinafter, an embodiment of a mammography apparatus according to the present invention will be described with reference to the accompanying drawings. In this process, the thickness of lines, size of elements, or the like illustrated in the drawings may have been exaggerated for clarity and convenience of description.

The terms which will be mentioned below are those defined in consideration of functions in the present invention, and the terms may vary according to intentions or practices of a user or an operator. Therefore, such terms should be defined on the basis of content throughout the present specification.

Figure 2:
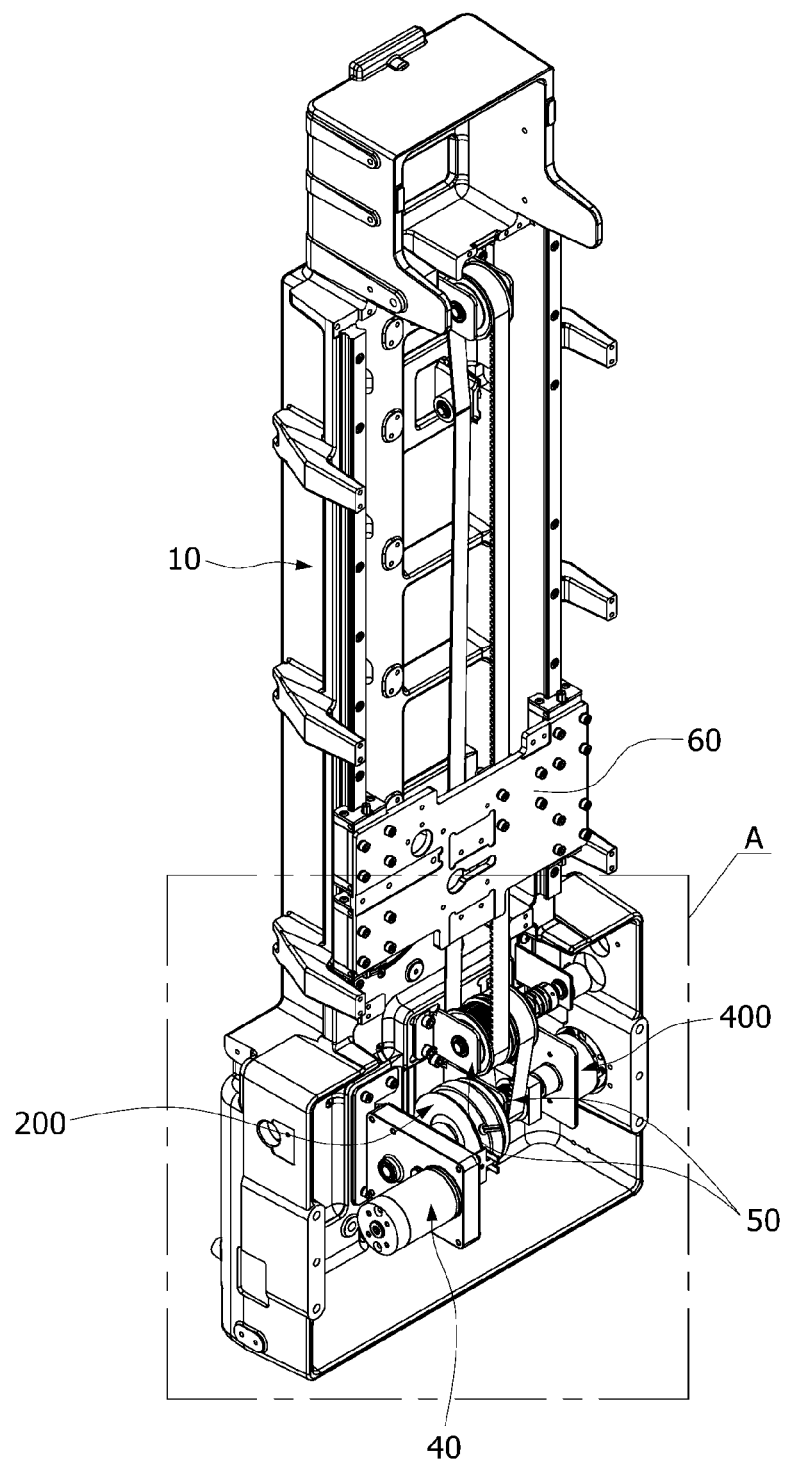
FIG. 2 is a perspective view illustrating the mammography apparatus according to an embodiment of the present invention.
Figure 3:
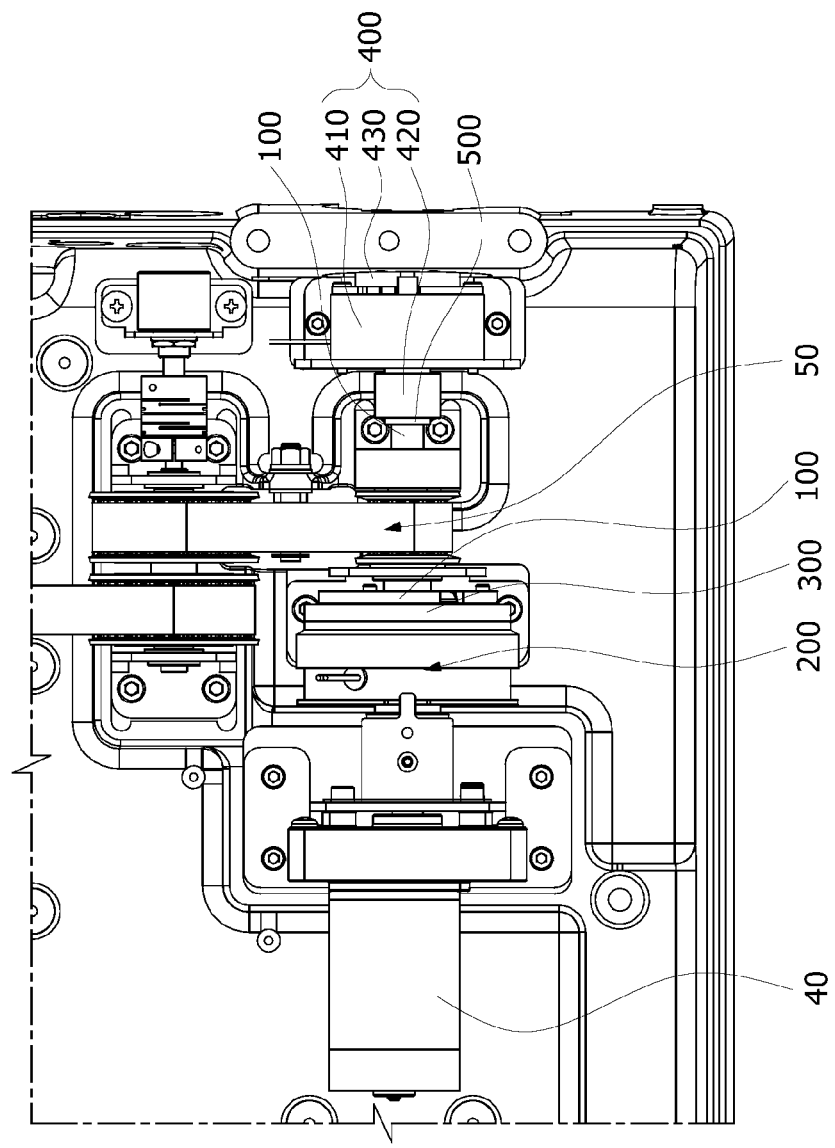
FIG. 3 is an enlarged view of portion A in FIG. 2.
Figure 4:
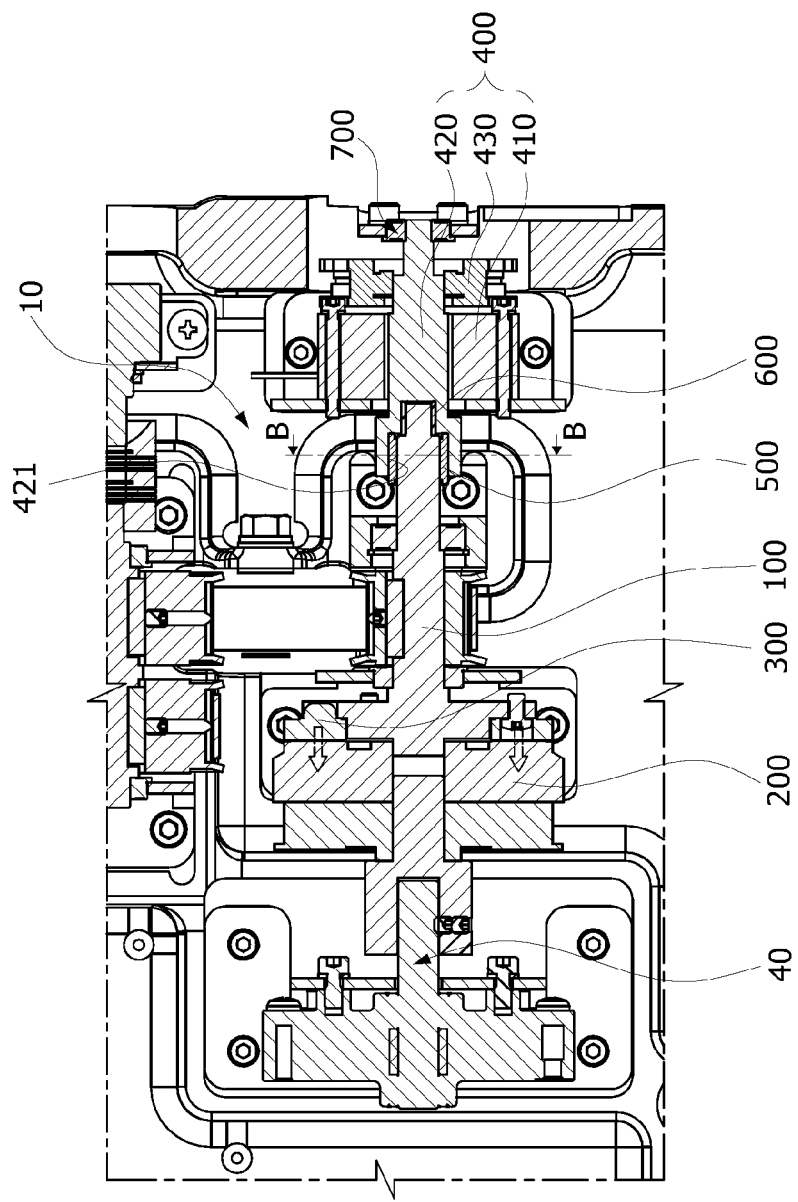
FIG. 4 is a side cross-sectional view illustrating a normal operation state of the mammography apparatus according to an embodiment of the present invention.
Figure 5:
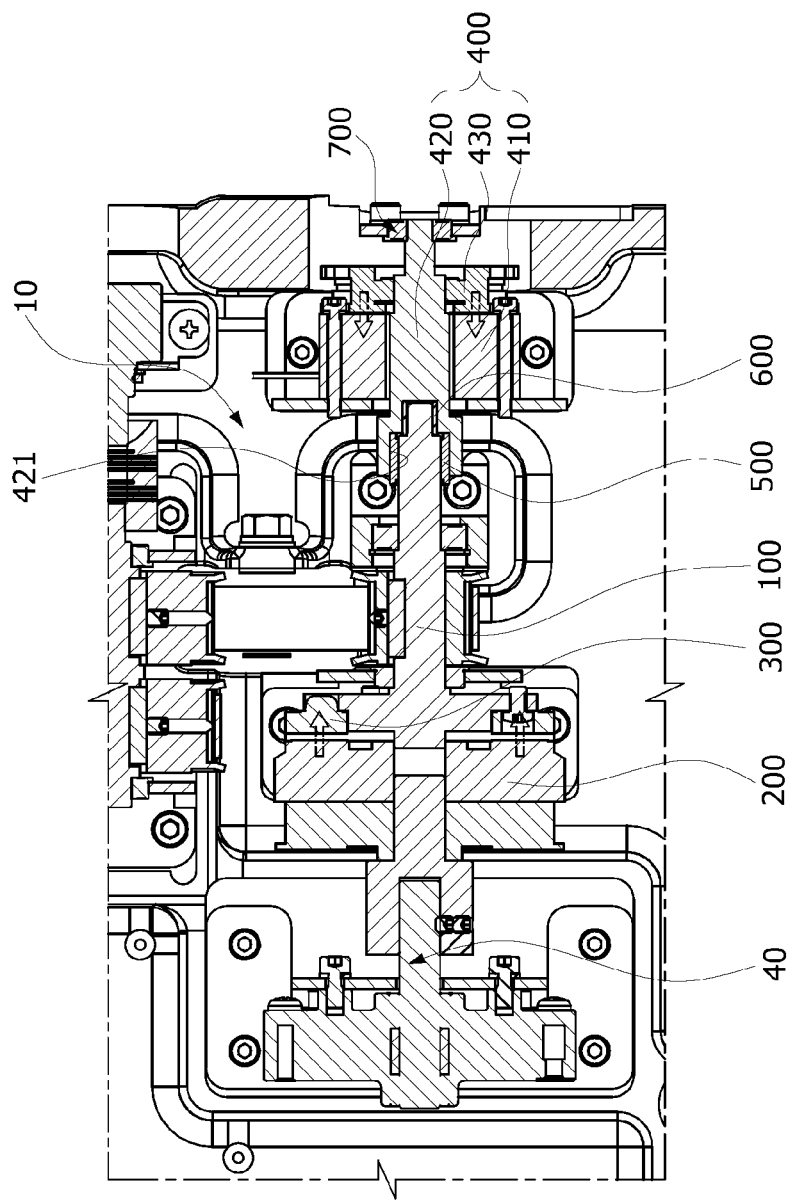
FIG. 5 is a side cross-sectional view illustrating a braking state of the mammography apparatus according to an embodiment of the present invention.
Figure 6:
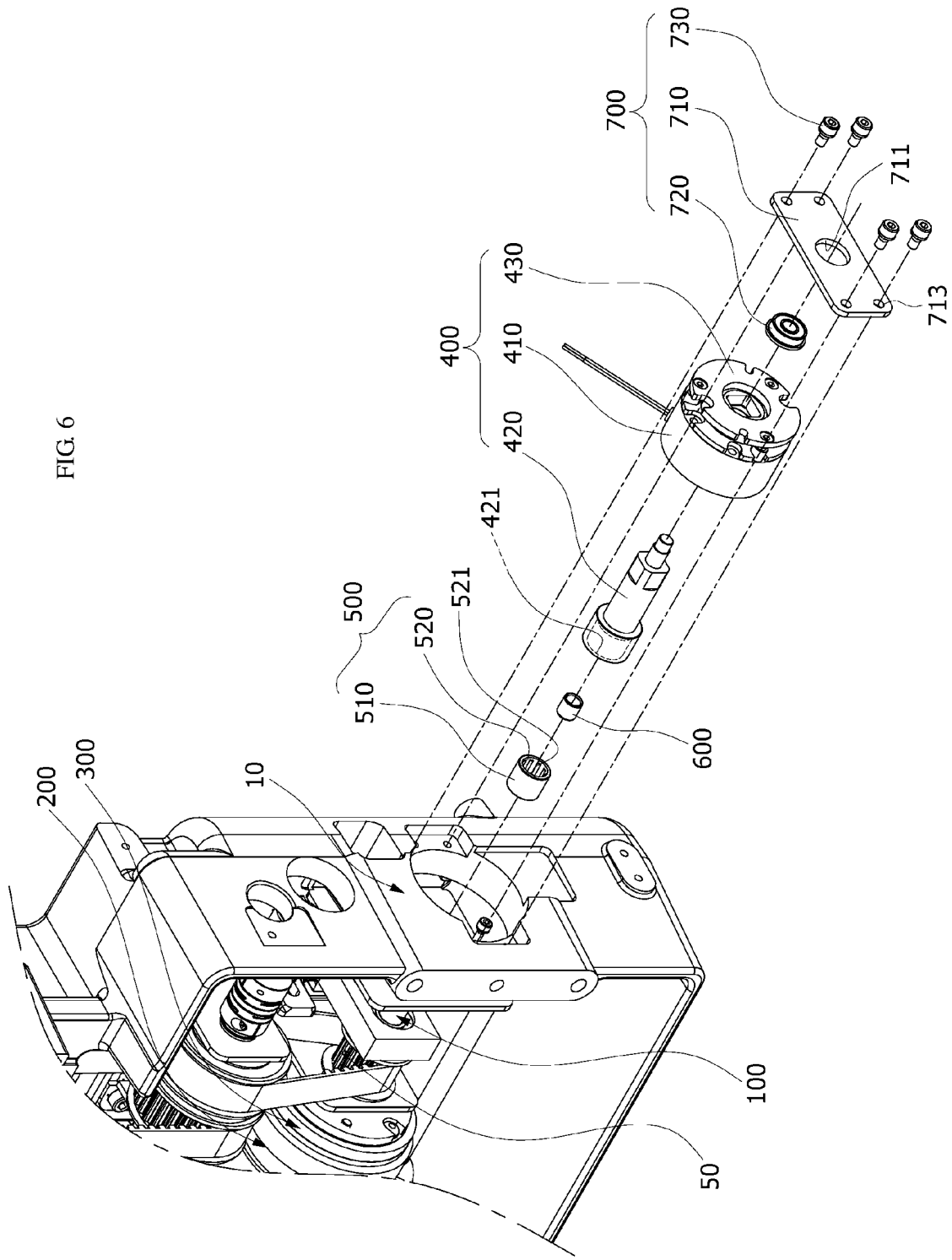
FIG. 6 is an exploded view illustrating the mammography apparatus according to an embodiment of the present invention.
Figure 7:
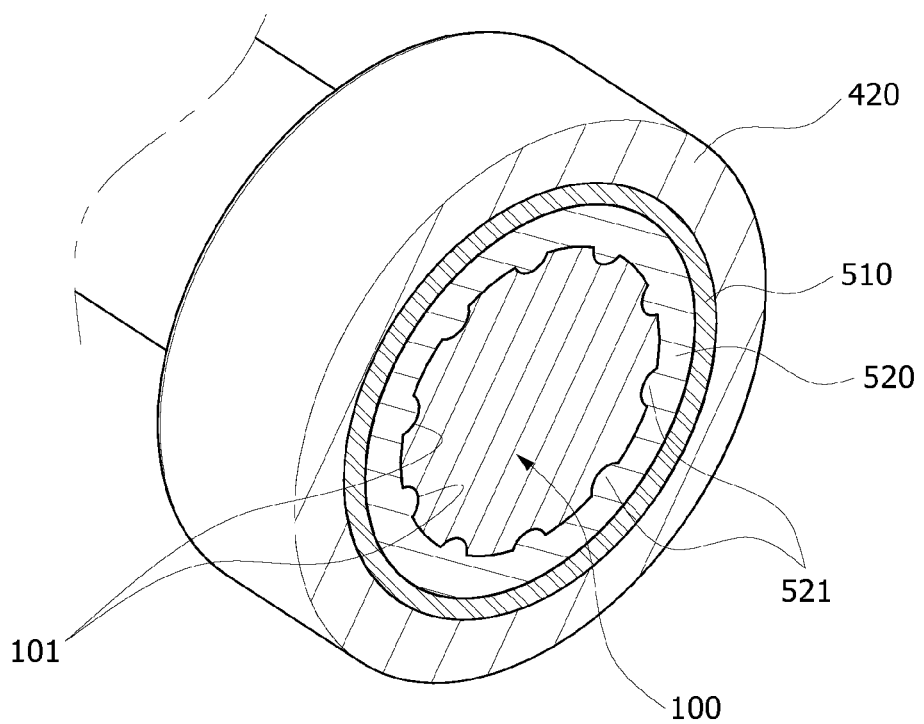
FIG. 7 is a normal cross-sectional view taken along line B-B in FIG. 4.

FIG. 1 is a side view illustrating a mammography apparatus according to an embodiment of the present invention. FIG. 2 is a perspective view illustrating the mammography apparatus according to an embodiment of the present invention. FIG. 3 is an enlarged view of portion A in FIG. 2. FIG. 4 is a side cross-sectional view illustrating a normal operation state of the mammography apparatus according to an embodiment of the present invention. FIG. 5 is a side cross-sectional view illustrating a braking state of the mammography apparatus according to an embodiment of the present invention. FIG. 6 is an exploded view illustrating the mammography apparatus according to an embodiment of the present invention. FIG. 7 is a normal cross-sectional view taken along line B-B in FIG. 4.

Referring to FIGS. 1 to 7, a mammography apparatus 1 according to an embodiment of the present invention includes a driving shaft 100, a loader 200, a power transmission unit 300, an emergency braking unit 400, a driving controller 500, a first supporter 600, and a second supporter 700.

The driving shaft 100 according to an embodiment of the present invention transmits power to a transfer unit 50. In the present invention, the power refers to rotary power, but embodiments are not limited thereto, and various modifications are possible. For example, the power may refer to linear power or the like.

The transfer unit 50 rotates clockwise or counterclockwise according to rotation of the driving shaft 100, and a lifting/lowering unit 60, which is coupled to the transfer unit 50, moves in a vertical direction (in FIG. 2) according to rotation of the transfer unit 50.

Referring to FIG. 1, a pressure unit 70 is coupled to the lifting/lowering unit 60 so that the pressure unit 70 presses a breast, which is a subject 5. The pressure unit 70 is lifted or lowered by interlocking with movement of the lifting/lowering unit 60 and presses the subject 5, which is disposed on an imaging unit 20, or is spaced apart from the subject 5.

Referring to FIG. 7, a coupling groove 101 is formed along an outer circumferential surface of the driving shaft 100 according to an embodiment of the present invention. The coupling groove 101 is formed in a shape which corresponds to the shape of a coupling protrusion 521, which is formed to protrude along an inner circumferential surface of a rotary part 520 which will be described below.

Therefore, the driving shaft 100 is spline-coupled to the driving controller 500, specifically the rotary part 520, an engaging force between the driving shaft 100 and the driving controller 500 is improved, and rotary power of the driving shaft 100 is transmitted to the rotary part 520.

In the present invention, the coupling groove 101 is formed in the driving shaft 100, and the coupling protrusion 521 is formed in the rotary part 520.

However, embodiments are not limited thereto, and various modifications are possible. For example, a coupling protrusion may be formed in the driving shaft 100 and a coupling groove may be formed in the rotary part 520 for spline-coupling between the driving shaft 100 and the driving controller 500.

Referring to FIGS. 3 to 5, the loader 200 according to an embodiment of the present invention is coupled to a driving unit 40 and rotates by receiving power, specifically rotary power, from the driving unit 40.

When the power transmission unit 300, which will be described below, comes in contact with the loader 200 due to an external force, specifically an electromagnetic force, the loader 200 transmits rotary power to the power transmission unit 300 and the driving shaft 100 coupled to the power transmission unit 300.

Referring to FIGS. 3 to 5, the power transmission unit 300 according to an embodiment of the present invention is coupled to one side (a left side in FIG. 4) of the driving shaft 100 and selectively comes in contact with the loader 200 due to an external force, specifically an electromagnetic force.

When power is supplied and an electromagnetic force is generated such that the power transmission unit 300 comes in contact with the loader 200, the rotary power transmitted from the driving unit 40 to the loader 200 is transmitted to the power transmission unit 300, and the driving shaft 100, which is coupled to the power transmission unit 300, rotates together with the power transmission unit 300.

Referring to FIGS. 2, 3, 4, and 6, the emergency braking unit 400 according to an embodiment of the present invention is coupled to the other side (a right side in FIG. 4) of the driving shaft 100 to be driven together with the driving shaft 100. The emergency braking unit 400 includes a housing 410, a braking shaft 420, and a braking main body 430.

Referring to FIG. 5, rotation of the emergency braking unit 400 according to an embodiment of the present invention is blocked when power supply is cut off.

Referring to FIGS. 3 to 5, the housing 410 according to an embodiment of the present invention is provided in a main body 10 and fixed therein.

Referring to FIGS. 4 to 6, the braking shaft 420 according to an embodiment of the present invention is rotatable inside the housing 410 and is connected to the driving shaft 100.

An insertion part 421 is formed inside the braking shaft 420, and the driving shaft 100 is inserted into the insertion part 421.

Referring to FIG. 4, when the driving shaft 100 rotates due to receiving power from the driving unit 40 while the mammography apparatus 1 operates normally due to power supplied thereto by connection between the braking shaft 420 and the driving shaft 100, the braking shaft 420 rotates together with the driving shaft 100.

Referring to FIGS. 4 to 6, the braking main body 430 according to an embodiment of the present invention is coupled to the braking shaft 420 and rotates together with the braking shaft 420.

Therefore, while the mammography apparatus 1 operates normally due to power supplied thereto, the braking main body 430 rotates together with the braking shaft 420 as the braking shaft 420, which has received rotary power from the driving shaft 100, rotates.

When power supply to the mammography apparatus 1 is cut off, the braking main body 430 moves toward the housing 410 (toward the left in FIG. 5) and comes in contact with the housing 410.

Therefore, friction occurs between the braking main body 430 and the housing 410, and due to the friction, rotations of the braking main body 430 and the braking shaft 420, which is coupled to the braking main body 430, are blocked.

Referring to FIGS. 5 and 6, the braking shaft 420 is inserted through the braking main body 430, and an inner surface of the braking main body 430 may be formed in the shape of a quadrilateral plane.

One side (a right end in FIG. 5) of the braking shaft 420 may also be formed in the shape of a quadrilateral plane to correspond to the shape of the inner surface of the braking main body 430.

Therefore, a separate fixing member, such as a key for engagement, is not required, slip between the braking shaft 420 and the braking main body 430 may be prevented, and braking performance may be enhanced.

Referring to FIGS. 4 to 7, the driving controller 500 according to an embodiment of the present invention causes a direction in which the driving shaft 100 is driven to be restricted to one direction.

Specifically, the driving controller 500 is provided between the driving shaft 100 and the emergency braking unit 400 so that a direction in which the driving shaft 100 rotates is restricted to either clockwise or counterclockwise.

The driving controller 500 is provided between an outer surface of the driving shaft 100 and an inner surface of the insertion part 421 formed in the braking shaft 420. The driving controller 500 includes a fixed part 510 and the rotary part 520.

In the present invention, the one direction refers to a direction in which the driving shaft 100 rotates that causes the lifting/lowering unit 60, which is coupled to the transfer unit 50, to move upward (in FIG. 2). The one direction refers to counterclockwise when the driving shaft 100 is seen from the left in FIG. 4.

Therefore, when power supply to the mammography apparatus 1 is cut off due to sudden power blackouts or the like, rotation of the driving shaft 100 in a direction in which the pressure unit 70 presses the subject 5, i.e., clockwise rotation of the driving shaft 100 that allows the lifting/lowering unit 60, to which the pressure unit 70 is coupled, to move downward (in FIG. 2), is blocked.

Since the driving controller 500 may rotate counterclockwise, the operator may move the lifting/lowering unit 60, to which the pressure unit 70 is coupled, upward (in FIG. 2) to cause the pressure unit 70 to be spaced apart from the subject 5.

In the present invention, the driving controller 500 restricts a direction in which the driving shaft 100 rotates to counterclockwise, but embodiments are not limited thereto, and various modifications are possible. For example, according to the design and structure of the mammography apparatus 1, a direction in which the driving shaft 100 rotates that causes the lifting/lowering unit 60 to move upward (in FIG. 2) may be restricted to clockwise or the like.

The fixed part 510 according to an embodiment of the present invention is coupled to an inner surface of the braking shaft 420. The fixed part 510 is fixed and coupled to the inner surface of the braking shaft 420 such that the fixed part 510 rotates together as the braking shaft 420 rotates.

Referring to FIG. 7, the fixed part 510 is formed to be hollow, and the rotary part 520 is provided inside the fixed part 510 and only rotates in one direction.

The rotary part 520 is coupled to the driving shaft 100 and only rotates in one direction inside the fixed part 510. In the present invention, the rotary part 520 only rotates counterclockwise, and clockwise rotation thereof is blocked.

Therefore, when power supply to the mammography apparatus 1 is blocked, movement of the lifting/lowering unit 60 may be blocked in a direction in which the pressure unit 70 presses the subject 5, i.e., downward (in FIG. 2), and the operator may move the lifting/lowering unit 60 upward (in FIG. 2).

Referring to FIG. 7, the coupling protrusion 521 is formed to protrude along an inner circumferential surface of the rotary part 520 according to an embodiment of the present invention. The coupling protrusion 521 is formed to extend in a longitudinal direction along the inner circumferential surface of the rotary part 520.

A plurality of coupling protrusions 521 are disposed at equal angular intervals about a central axis of the rotary part 520. The shape of the coupling protrusion 521 corresponds to the shape of the coupling groove 101 which is formed along the outer circumferential surface of the driving shaft 100.

Therefore, the driving shaft 100 is inserted into the rotary part 520, and an engaging force between the driving shaft 100 and the rotary part 520 is enhanced.

Referring to FIGS. 4 to 6, the first supporter 600 according to an embodiment of the present invention is disposed to be spaced apart from the driving controller 500 and is provided between the insertion part 421 and the driving shaft 100.

Specifically, the first supporter 600 is provided between an inner surface of the insertion part 421 and an outer surface of the driving shaft 100 such that the first supporter 600 reduces friction between the inner surface of the insertion part 421 and the outer surface of the driving shaft 100 and prevents damages to the driving shaft 100 and the braking shaft 420 due to friction.

In the present invention, the first supporter 600 is formed as a hollow bush, but embodiments are not limited thereto, and various modifications are possible. For example, the first supporter 600 may be formed as a bearing to support a rotating load of the driving shaft 100 and reduce friction.

Referring to FIGS. 4 to 6, the second supporter 700 according to an embodiment of the present invention is provided in the main body 10.

The driving shaft 100 is connected to one end (a left end in FIG. 4) of the braking shaft 420, and the second supporter 700 is coupled to the other side (a right end in FIG. 4) of the braking shaft 420.

The second supporter 700 may support a rotating load that acts on a right end (in FIG. 5) of the braking shaft 420 and reduce friction.

Referring to FIG. 6, the second supporter 700 according to an embodiment of the present invention includes a support plate 710, a support main body 720, and an engaging member 730.

Referring to FIG. 6, the support plate 710 is provided in the main body 10 and includes a support hole 711 formed therein. The support main body 720 surrounds the braking shaft 420 and is coupled to an inner surface of the support hole 711.

In the present invention, the support main body 720 is formed as a bearing, but embodiments are not limited thereto, and various modifications are possible. For example, the support main body 720 may be formed as a bush which is provided to be rotatable inside the support hole 711 and is hollow so that friction between the braking shaft 420 and the support plate 710 is reduced.

Referring to FIG. 6, the engaging member 730 according to an embodiment of the present invention engages the main body 10 and the support plate 710 by passing therethrough and prevents detachment of the support plate 710 from the main body 10.

Hereinafter, an action principle and advantageous effects of the mammography apparatus 1 according to an embodiment of the present invention will be described.

Referring to FIGS. 1 to 7, the mammography apparatus 1 according to an embodiment of the present invention includes the driving shaft 100, the loader 200, the power transmission unit 300, the emergency braking unit 400, the driving controller 500, the first supporter 600, and the second supporter 700.

Referring to FIG. 1, a breast, which is the subject 5, is disposed on the imaging unit 20, and the pressure unit 70, which is coupled to the lifting/lowering unit 60, presses the subject 5 as the lifting/lowering unit 60 moves downward (in FIG. 1).

Referring to FIG. 1, an irradiation unit 30 irradiates the subject 5 disposed on the imaging unit 20 with radiation R. X-rays are used as the radiation R, but embodiments are not limited thereto, and various modifications are possible as long as the radiation R is allowed to be used for medical purposes. For example, the radiation R may be gamma rays or the like.

Referring to FIGS. 2 to 4, the driving shaft 100 is coupled to the transfer unit 50 and transmits power, specifically rotary power, to the transfer unit 50.

Referring to FIG. 4, the transfer unit 50 rotates as the driving shaft 100, which has received rotary power from the driving unit 40, rotates, and the lifting/lowering unit 60, which is coupled to the transfer unit 50, moves in the vertical direction (in FIG. 2) as the transfer unit 50 rotates clockwise or counterclockwise.

Referring to FIGS. 3 and 4, the loader 200 is disposed outside the driving shaft 100 and rotates by receiving power, specifically rotary power, from the driving unit 40.

The power transmission unit 300 rotates together with the driving shaft by being coupled thereto and comes into contact with the loader 200 due to an electromagnetic force which is generated due to receiving an electrical signal from the outside.

Therefore, the power transmission unit 300 and the driving shaft 100 rotate by receiving power from the driving unit 40.

As the driving shaft 100 rotates clockwise or counterclockwise, the transfer unit 50 rotates, the lifting/lowering unit 60, which is coupled to the transfer unit 50, is lifted or lowered, and the pressure unit 70, which is coupled to the lifting/lowering unit 60, presses the subject 5 disposed on the imaging unit 20 or is spaced apart from the subject 5.

Referring to FIGS. 2 to 5, when power supply is cut off, rotation of the emergency braking unit 400 stops. Specifically, the emergency braking unit 400 includes the housing 410, the braking shaft 420, and the braking main body 430.

Referring to FIG. 4, while the mammography apparatus 1 operates normally, the braking main body 430 is spaced apart from the housing 410 and rotates by interlocking with the braking shaft 420, which rotates by receiving rotary power from the driving shaft 100.

Referring to FIG. 5, when power supply to the mammography apparatus 1 is cut off due to an accident such as power blackouts during operation of the mammography apparatus 1, a magnetic force is generated in the housing 410, and the braking main body 430 moves to the left (in FIG. 5) due to the magnetic force and comes in contact with the housing 410.

Friction occurs due to contact between the braking main body 430 and the housing 410, and rotations of the braking main body 430 and the braking shaft 420, which is coupled to the braking main body 430, are blocked.

Referring to FIG. 5, when power supply to the mammography apparatus 1 is cut off, as the electromagnetic force of the loader 200 disappears, the power transmission unit 300 is spaced apart from the loader 200, and the pressure unit 70 and the lifting/lowering unit 60 move downward (in FIG. 1) due to gravity.

When the pressure unit 70 moves downward, there is a problem in that the subject 5 disposed on the imaging unit 20 is continuously pressed and pain may be caused.

Referring to FIGS. 4 to 6, the driving controller 500 according to an embodiment of the present invention is connected to the driving shaft 100 and restricts a direction in which the driving shaft 100 rotates to one direction.

Specifically, the driving controller 500 is formed so that rotation of the driving shaft 100 is blocked in a direction in which the pressure unit 70 moves downward, i.e., clockwise when the transfer unit 50 is seen from the left (in FIG. 4), and is only allowed in a direction opposite thereto, i.e., counterclockwise, so that the lifting/lowering unit 60 and the pressure unit 70 move upward.

Therefore, as the power supply is cut off, the pressure unit 70 is prevented from pressing the subject 5, which is disposed on the imaging unit 20, further, and the operator is allowed to manually move the pressure unit 70 upward.

In addition, even when the operator moves the pressure unit 70 upward (in FIG. 2) to cause the pressure unit 70 to be spaced apart from the subject 5 which is disposed on the imaging unit 20, the driving controller 500 may prevent the pressure unit 70 from falling downward (in FIG. 2).

Referring to FIG. 4, when power is supplied to the mammography apparatus 1, the power transmission unit 300 receives power from the driving unit 40 due to coming in contact with the loader 200 such that the driving shaft 100 rotates, and the braking main body 430 is spaced apart from the housing 410 such that the braking shaft 420 rotates inside the housing 410 by interlocking with the rotation of the driving shaft 100.

Referring to FIG. 5, when power of the mammography apparatus 1 is cut off, the braking main body 430 moves to the left (in FIG. 5) due to the magnetic force generated in the housing 410 and comes into contact with the housing 410, and rotation of the braking main body 430 stops.

Since the rotation of the braking main body 430 is blocked, the rotation of the braking shaft 420, which is coupled to the inside of the braking main body 430, is also blocked.

Referring to FIGS. 4 to 6, one end of the driving shaft 100 is inserted into the insertion part 421 formed in the braking shaft 420, and the driving controller 500 is provided between the outer surface of the driving shaft 100 and the inner surface of the insertion part 421 formed in the braking shaft 420.

Referring to FIG. 7, the driving controller 500 includes the fixed part 510 and the rotary part 520. The fixed part 510 is coupled to the braking shaft 420, specifically, the inner surface of the insertion part 421, and the rotary part 520 is provided to be rotatable on an inner surface of the fixed part 510.

When power supply to the mammography apparatus 1 is cut off, since the braking main body 430 comes in contact with the housing 410, rotations of the braking main body 430 and the braking shaft 420, which is coupled to the braking main body 430, are blocked.

As the rotation of the braking shaft 420 is blocked, the driving shaft 100 rotates inside the braking shaft 420, specifically, the insertion part 421, relative thereto, and due to the driving controller 500, a direction in which the driving shaft 100 rotates is restricted to one direction.

Specifically, for the lifting/lowering unit 60 to be moved upward, rotation is allowed in a direction in which the driving shaft 100, which is coupled to the transfer unit 50, rotates (counterclockwise when seen from the left in FIG. 4) and is blocked in a direction opposite thereto.

In other words, for the lifting/lowering unit 60 to be moved downward, rotation is only allowed in a direction in which the transfer unit 50 and the driving shaft 100 coupled thereto rotate (clockwise when seen from the left in FIG. 4).

Therefore, when the power supply is cut off, downward movement of the pressure unit 70 may be blocked, and a casualty that occurs due to the pressure unit 70 continuously pressing the subject 5 may be prevented.

Referring to FIGS. 4 and 5, due to being provided between the insertion part 421 and the driving shaft 100, the first supporter 600 may support a rotating load that acts on one end (a right end in FIG. 4) of the driving shaft 100 and may prevent wear and damages due to friction which occurs between the driving shaft 100 and the braking shaft 420.

Referring to FIGS. 4 and 5, the second supporter 700 according to an embodiment of the present invention is provided in the main body 10. The driving shaft 100 is connected to one end (a left end in FIG. 4) of the braking shaft 420, and the second supporter 700 is coupled to the other side (a right end in FIG. 4) of the braking shaft 420.

Therefore, the second supporter 700 may support a rotating load that acts on the other end (the right end in FIG. 4) of the braking shaft 420 and may prevent wear due to friction which occurs between the braking shaft 420 and the main body 10.

According to the mammography apparatus of the present invention, in case of emergency such as when power supply is cut off, driving of an emergency braking unit stops so that movement of a pressure unit toward a subject can be prevented.

In addition, a direction in which a driving shaft is driven is restricted to one direction due to a driving controller, and the pressure unit, which is lifted and lowered by being connected to the driving shaft, is prevented from continuously pressing the subject. In this way, the subject can be protected.

In addition, falling of the pressure unit toward the subject can be prevented even after the operator causes the pressure unit to be spaced apart from the subject.

In addition, a coupling protrusion is inserted into a coupling groove so that an engaging force between the driving shaft and the driving controller can be enhanced.

In addition, a load of the driving shaft can be supported due to a first supporter, and friction which occurs between the driving shaft and a braking shaft can be reduced.

In addition, a load of the braking shaft can be supported due to a second supporter, and friction which occurs between a main body and the braking shaft can be reduced.

The present invention has been described above with reference to embodiments illustrated in the drawings, but the embodiments are merely illustrative, and one of ordinary skill in the art should understand that various modifications may be made to the embodiments, and other equivalent embodiments are possible. Therefore, the technical scope of the present invention should be defined by the claims below.

What is claimed is:

1. A mammography apparatus comprising:
    a loader configured to be driven by receiving power from a driving unit;
    a power transmission unit configured to selectively come in contact with the loader due to an external force;
    a driving shaft coupled to the power transmission unit and configured to transmit power to a transfer unit;
    an emergency braking unit coupled to the driving shaft to be driven together with the driving shaft, and configured to stop being driven when power supply is cut off; and
    a driving controller provided between the driving shaft and the emergency braking unit so that a direction in which the driving shaft is driven is restricted to one direction,
    wherein the power transmission is coupled to one side of the driving shaft and the emergency braking unit is coupled to the other side of the driving shaft.

2. The mammography apparatus of claim 1, wherein the emergency braking unit comprises:
    a housing provided in a main body;
    a braking shaft configured to be rotatable inside the housing and connected to the driving shaft; and
    a braking main body coupled to the braking shaft and configured to rotate together with the braking shaft,
    wherein, when power supply is cut off, the braking main body moves toward the housing and comes into contact with the housing.

3. The mammography apparatus of claim 2, wherein:
    an insertion part is formed in the braking shaft;
    the driving shaft is disposed inside the insertion part; and
    the driving controller is provided between the braking shaft and the driving shaft.

4. The mammography apparatus of claim 2, wherein the driving controller comprises:
    a fixed part coupled to an inner surface of the braking shaft; and
    a rotary part coupled to the driving shaft and configured to only rotate in one direction inside the fixed part.

5. The mammography apparatus of claim 4, wherein:
    a coupling protrusion is formed to protrude along an inner circumferential surface of the rotary part; and
    a coupling groove is formed along an outer circumferential surface of the driving shaft to correspond to a shape of the coupling protrusion.

6. The mammography apparatus of claim 3, further comprising a first supporter disposed to be spaced apart from the driving controller and provided between the insertion part and the driving shaft.

7. The mammography apparatus of claim 2, further comprising a second supporter provided in the main body, wherein the driving shaft is connected to one end of the braking shaft, and the second supporter is coupled to the other side of the braking shaft.

* * * * *